United States Patent [19]
Houston et al.

[11] Patent Number: 5,689,323
[45] Date of Patent: Nov. 18, 1997

[54] DECENTERED NONCORRECTIVE LENS FOR EYEWEAR

[75] Inventors: Malcolm Neal Houston, Foothill Ranch, Calif.; James H. Jannard, Double Island, Wash.; Carlos D. Reyes, Mission Viejo, Calif.

[73] Assignee: Oakley, Inc., Foothill Ranch, Calif.

[21] Appl. No.: 706,564

[22] Filed: Sep. 5, 1996

Related U.S. Application Data

[62] Division of Ser. No. 567,434, Dec. 5, 1995, Pat. No. 5,648,832.

[51] Int. Cl.$^6$ .................................................. G02C 13/00
[52] U.S. Cl. .................................................. 351/41; 351/178
[58] Field of Search .................................. 351/41, 44, 159, 351/177, 178

[56] References Cited

U.S. PATENT DOCUMENTS

| | | | |
|---|---|---|---|
| 1,332,410 | 3/1920 | Potts | 351/159 |
| 1,354,040 | 9/1920 | Hammon | 351/159 |
| 1,536,828 | 5/1925 | Drescher | 351/159 |
| 1,619,341 | 3/1927 | Gagnon | 351/159 |
| 1,697,030 | 1/1929 | Tillyer | 351/159 |
| 1,741,536 | 12/1929 | Rayton | 351/159 |
| 1,910,466 | 5/1933 | Glancy | 351/159 |
| 1,942,400 | 1/1934 | Glancy | 351/159 |
| 2,406,608 | 8/1946 | Joyce | 2/14 |
| 2,442,849 | 6/1948 | Glazer | 351/159 |
| 3,229,303 | 1/1966 | Jonassen | 2/14 |
| 4,271,537 | 6/1981 | Bowlus et al. | 2/424 |
| 4,271,538 | 6/1981 | Montesi et al. | 2/439 |
| 4,515,448 | 5/1985 | Tackles | 35/41 |
| 4,613,217 | 9/1986 | Fuerter et al. | 351/176 |
| 4,741,611 | 5/1988 | Burns | 351/44 |
| 4,761,315 | 8/1988 | Logan et al. | 351/159 X |
| 4,859,048 | 8/1989 | Jannard | 351/159 |
| 4,867,550 | 9/1989 | Jannard | 351/47 |
| 5,050,979 | 9/1991 | Shinohara | 351/159 |
| 5,131,101 | 7/1992 | Chin | 2/424 |
| 5,208,614 | 5/1993 | Jannard | 351/41 |
| 5,390,369 | 2/1995 | Tubin | 2/12 |
| 5,541,674 | 7/1996 | Jannard | 351/41 |
| 5,555,038 | 9/1996 | Conway | 351/41 |

FOREIGN PATENT DOCUMENTS

| | | |
|---|---|---|
| 0456321 | 5/1949 | Canada . |
| 0 121 018 A2 | 10/1984 | European Pat. Off. . |
| 2 626 683 | 8/1989 | France . |
| 1765802A1 | 9/1992 | Switzerland . |
| 2 278 459 | 11/1994 | United Kingdom . |

*Primary Examiner*—Huy Mai
*Attorney, Agent, or Firm*—Knobbe, Martens, Olson & Bear, LLP

[57] ABSTRACT

Disclosed is an optically corrected lens for nonprescription, dual lens eyeglasses. In a preferred embodiment, the anterior surface of the lens lies on a portion of a first sphere having a first center. The posterior surface of the lens lies on the surface of a second sphere having a second center. The first and second centers are offset from one another to provide a tapered lens. The lens is oriented on the head of the wearer by a frame that maintains the lens in a position such that a line drawn through the first and second centers is maintained substantially in parallel to the normal sight line of the wearer. Methods of making the lenses, and eyewear incorporating the lenses, are also disclosed.

15 Claims, 7 Drawing Sheets

LINE OF SIGHT

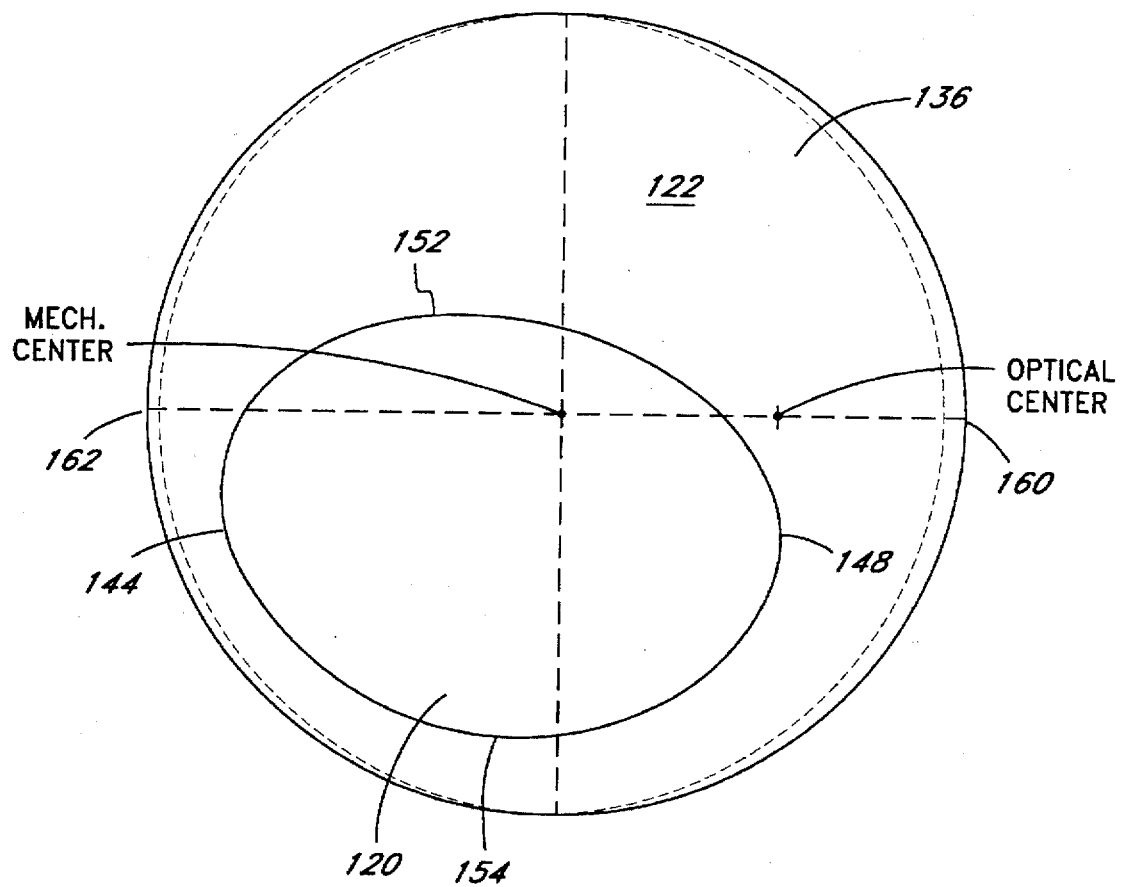

DECENTERED NONCORRECTIVE LENS FOR EYEWEAR

This application is a divisional U.S. patent application Ser. No. 08/567,434, filed Dec. 5, 1995, now U.S. Pat. No. 5,648,832.

The present invention relates generally to lenses used eyewear, and more particularly to a decentered, noncorrective lens to reduce optical distortion.

BACKGROUND OF THE INVENTION

A wide variety of improvements have been made in recent years in the eyewear field, particularly with respect to eyewear intended for use in active sports or as fashion sunglasses. These improvements have been incorporated into eyewear having a unitary lens, such as the "Blades®" design (Oakley, Inc.) the "M Frame®" line (Oakley, Inc.), and the "Zero®" line also produced by Oakley, Inc. These eyewear designs accomplish a variety of functional advantages, such as maximizing interception of peripheral light, reducing optical distortion and increasing the wearer's comfort level, compared to previous active sport eyewear.

The unitary lens of the "Blades®" eyewear incorporates the cylindrical geometry disclosed, for example, in U.S. Pat. No. 4,859,048, issued to Jannard. This geometry allows the lens to closely conform to the wearer's face and intercept light, wind, dust, etc. from directly in front of the wearer (anterior direction) and peripherally (lateral direction). See also U.S. Pat. No. 4,867,550 to Jannard (toroidal lens geometry).

Although the early unitary lens systems provided a full side-to-side range of vision and good lateral eye protection, the potential for optical distortion still exists. In a unitary lens system, for example, the angle of incidence from the wearer's eye to the posterior lens surface changes as the wearer's sight line turns in the lateral direction. This results in disparate refraction between light entering closer to the front of the lens and peripheral light entering at the lateral ends. To address this source of prismatic distortion, U.S. Pat. No. 4,859,048 discloses tapering the thickness of the lens from the medial portion toward the lateral edge.

Prior art eyewear has also employed dual lens systems in which two separate lenses are mounted along a front frame. In the early dual lens eyeglass systems, each of the right and left lenses were roughly co-planar in the as-worn configuration. Thus, the sight line of the wearer, when looking straight ahead, generally crossed the posterior surface of the lens at a normal to the lens surface in the optical zone. One of the disadvantages of this lens configuration was that the eyeglasses provided essentially no lateral eye protection without the use of special modifications, such as vertically elongated earstems or side attachments.

Dual lens systems were thereafter developed in which the lateral edge of each lens curved rearwardly from the frontal plane, and around the side of the wearer's head to provide a lateral wrap similar to that achieved by the high wrap unitary lens systems. Although the dual lens eyeglasses with significant wrap provided lateral eye protection, the lens curvature generally introduced measurable prismatic distortion through the wearer's angular range of vision. This was particularly pronounced in lenses comprising low index of refraction materials. In addition, although high base curvatures (e.g. base 6 or higher) are sometimes desirable to optimize wrap while maintaining a low profile, such lenses have not been practical in the past due to the relatively high level of prismatic distortion.

Thus, there remains a need for a high base nonprescription lens for use in dual lens eyewear which can intercept light over essentially the full angular range of vision while at the same time minimize optical distortion throughout that range.

SUMMARY OF THE INVENTION

There is provided in accordance with one aspect of the present invention, an eyeglass lens for use in noncorrective dual lens eyewear. The eyeglass lens is utilized in combination with a frame to support the lens in the path of the wearer's normal line of sight.

The lens comprises a lens body, having a front surface, a rear surface, and a thickness therebetween.

The front surface of the lens conforms to a portion of the surface of a solid geometric shape. Preferably, the front surface of the lens conforms substantially to a portion of the surface of a first sphere having a first center. The rear surface of the lens conforms substantially to a portion of the surface of a solid geometric shape, which may be the same or different than that conforming to the front surface. Preferably, the rear surface conforms substantially to a portion of the surface of a second sphere having a second center.

The first and second centers are offset from one another to taper the lens thickness. The lens is mounted in the frame such that a line drawn through the first and second centers is maintained generally in parallel with the wearer's normal line of sight.

The lens may be cut from a lens blank, or formed directly into its final configuration such as by injection molding or other techniques known in the art. Preferably, the lens is oriented on the head of a wearer by the eyeglass frame such that the normal sight line of the wearer crosses the anterior surface of the lens at an angle of greater than about 95°, and preferably within the range of from about 100° to about 120°, while maintaining the optical centerline of the lens in a generally parallel relationship with the normal sight line of the wearer. The optical centerline of the lens may or may not pass through the lens.

Methods of making the lens of the present invention are also disclosed.

Further features and advantages of the present invention will become apparent from the detailed description of preferred embodiments which follows, when considered together with the attached claims and drawings.

BRIEF DESCRIPTION OF THE DRAWINGS

FIG. 12 is a front elevational view of the lens and lens blank of FIG. 6, rotated to project the mechanical centerline of the blank normal to the page.

DETAILED DESCRIPTION OF THE PREFERRED EMBODIMENTS

Although the preferred embodiments will be discussed below in terms of lenses having "spherical" front and rear surfaces (surfaces which conform substantially to a portion of the surface of a sphere), it will be understood by those having ordinary skill in the art that the invention may also be applicable to lenses having different surface geometries. Additionally, it will be understood that the present invention has application to lenses of many front elevational shapes and orientations in the as worn position beyond those illustrated herein.

Figure 1:
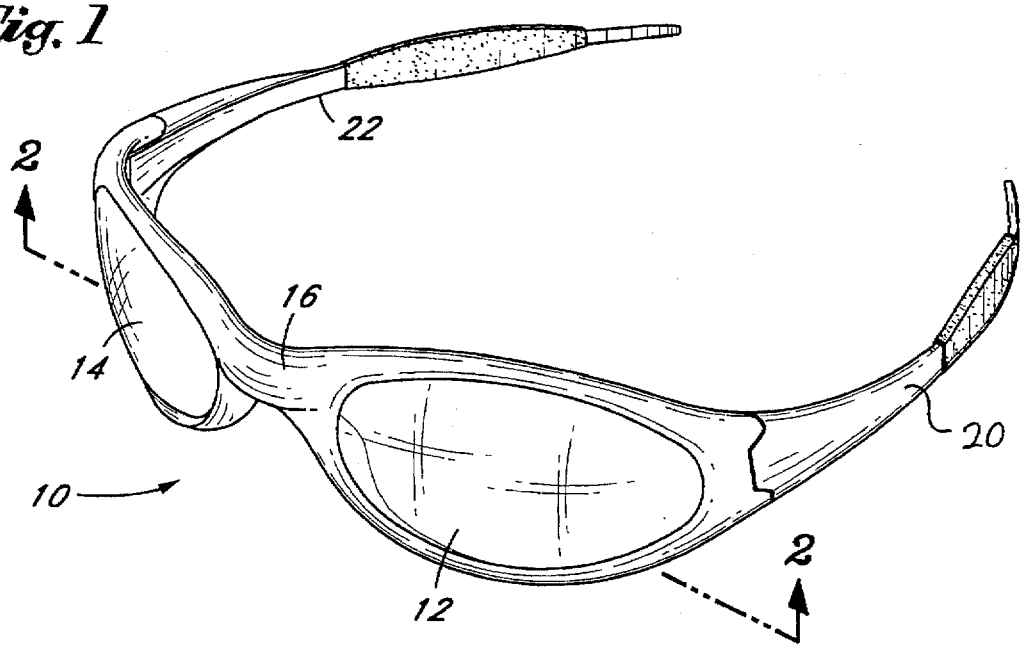
FIG. 1 is a perspective view of eyewear incorporating taper corrected lenses made in accordance with an embodiment of the present invention.
Figure 2:
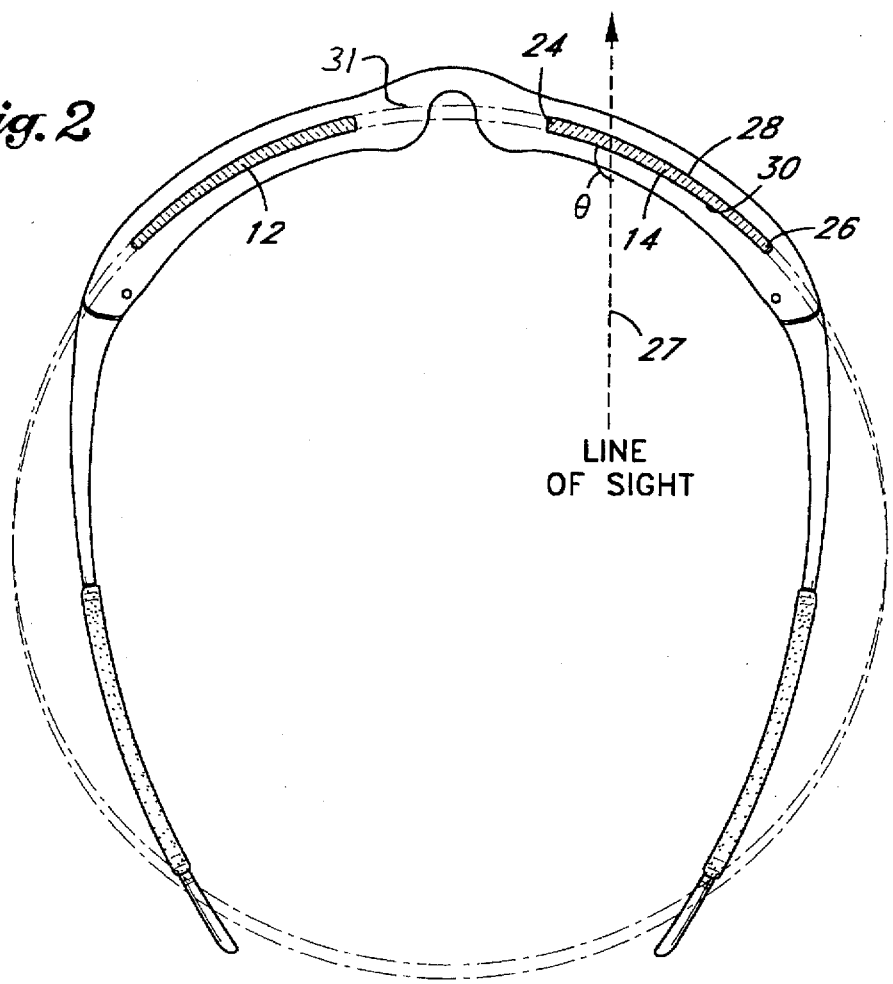
FIG. 2 is a cross-sectional view taken along the lines 2—2 of FIG. 1.

Referring to FIGS. 1 and 2, there is illustrated an eyeglass 10, such as a sunglass having first and second lenses 12, 14 constructed in accordance with an embodiment of the present invention. Although the invention is illustrated in the context of an eyeglass design marketed by Oakley under the Eye Jackets™ name, the present invention relates solely to the lens curvature, taper, and orientation on the head of the wearer. Therefore the particular lens shape revealed in FIG. 1 is not critical to the invention. Rather, lenses of many other shapes and configurations may be constructed which incorporate the present invention as will become apparent based upon the disclosure herein.

Similarly, the particular mounting frame 16 shown is not essential to the present invention. The frame 16 may bound only the bottom edge(s) of the lenses 12, 14, only the top edges, or the entire lenses as illustrated. Alternatively, the frame 16 can bound any other portions of the lenses as will be evident to those of skill in the art. Frameless eyeglasses can also be constructed in accordance with the present invention, as long as the lens orientation on the head of the wearer is substantially maintained in a predetermined relationship to the normal sight line as will be discuss, below. Preferably, though, lenses 12, 14 are each mounted in an annular orbital as shown.

A pair of earstems 20, 22 pivotally attach to the frame 16. Alternatively, the earstems 20, 22 may attach directly to the lenses 12, 14. The frame may comprise of any of a variety of metals, composites or relatively rigid, molded thermoplastic materials which are well known in the art, and may be transparent or any of a variety of colors. Injection molding, machining and other construction techniques are well known in the art.

Lenses in accordance with the present invention can be manufactured by any of a variety of processes well known in the art.

Typically, high optical quality lenses are cut from a preformed injection molded lens blank. Since the right and left lenses are preferably mirror images of each other, only the right lens will generally be discussed below. Alternatively, the lens can be molded directly into its final shape and size, to eliminate the need for post molding cutting steps.

Preferably, the lens, or the lens blank from which it is cut, is injection molded and comprises a relatively rigid and optically acceptable material, such as polycarbonate. Other polymeric lens materials can also be used, such as CR-39 and a variety of high index plastics which are known in the art. The decentered taper correction of the present invention may also be applicable to glass lenses, although the need for correction in the present context is generally more pronounced in nonglass materials.

If the lens is to be cut from a lens blank, the taper and curvature of a carefully preselected portion of the molded lens blank is transferred to the lens in accordance with a preferred manufacturing process described below. Preferably, the frame is provided with a slot or other attachment structure that cooperates with the molded curvature of the lens to minimize deviation from, and even improve retention of the as-molded curvature.

Alternatively, the lens or lens blank can be stamped or cut from generally planar tapered sheet stock and then bent into the curved configuration in accordance with the present invention. This curved configuration can then be maintained by the use of a relatively rigid, curved frame, or by heating the curved sheet to retain its curved configuration, as is well known in the thermoforming art.

Most preferably, the curvature of both surfaces of the lens are created in the lens blank molding and polishing processes, and the lens shape is cut from the blank in accordance with the invention as described below.

Referring to FIG. 2, the lens 14 of the present invention is characterized in a horizontal plane by a generally arcuate shape, extending from a medial edge 24 throughout at least a portion and preferably substantially all of the wearer's range of vision to a lateral edge 26. The arc length of the lens from the medial edge 24 to the lateral edge 26 in a dual lens system will generally be within the range of from about 1½ inches to about 3 inches, and preferably within the range of from about 2 inches to about 3 inches. In one preferred embodiment, the arc length of the lens is about 2⅜ inches.

Although the outer surfaces of the lenses 12, 14 appear to be illustrated as lying on a common circle 31, the right and left lenses will generally be canted such that the medial edge of each lens will fall outside of the circle 31 and the lateral edges will fall inside of the circle 31. such canting of the lens increases the angle θ (FIG. 2) and increases the desirability of the optical correction achieved by the present invention.

When worn, the lens 14 should at least extend across the wearer's normal line of sight 27, and preferably substantially across the wearer's peripheral zones of vision. As used herein, the wearer's normal line of sight shall refer to a line projecting straight ahead of the wearer's eye, with substantially no angular deviation in either the vertical or horizontal planes as illustrated by line 130 in FIGS. 9 and 10.

The lens 14 is provided with an anterior surface 28, a posterior surface 30, and a varying thickness therebetween. The thickness of the lens 14 in the region of the medial edge 24 for a polycarbonate lens is generally within the range of from about 1 mm to about 2.5 mm, and preferably in the range of from about 1.5 mm to about 1.8 mm. In a preferred embodiment, the thickest portion of the lens 14 is at or about the optical centerline, and is about 1.65 mm.

Preferably, the thickness of the lens 14 tapers smoothly, though not necessarily linearly, from the maximum thickness proximate the medial edge 24 to a relatively lesser thickness at the lateral edge 26. The thickness of the lens near the lateral edge 26 is generally within the range of from about 0.635 mm to about 1.52 mm, and, preferably, within the range of from about 0.762 mm to about 1.27 mm. In one preferred polycarbonate embodiment, the lens has a minimum thickness in the lateral zone of about 1.15 mm. The minimum thickness at lateral edge 26 is generally governed by the desired impact resistance of the lens.

Figure 3:
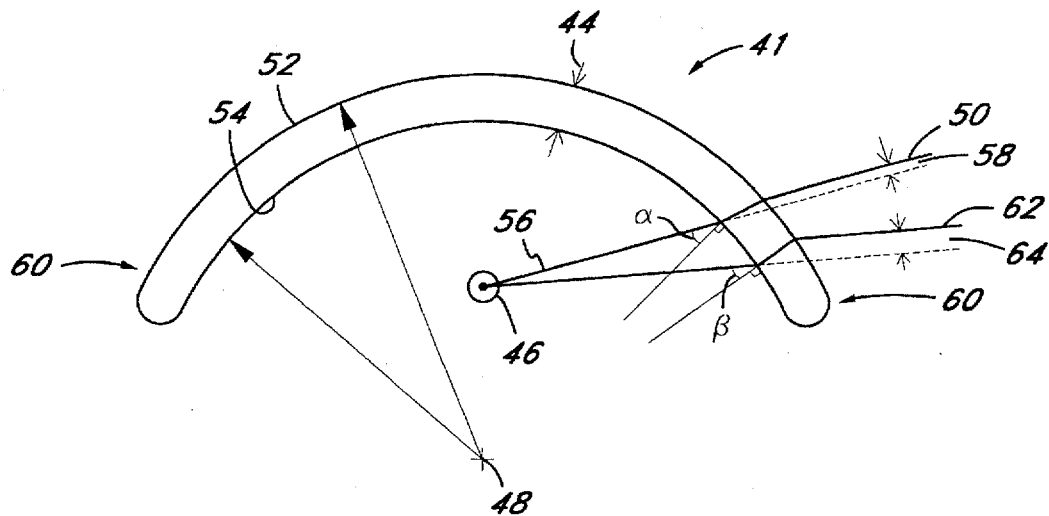
FIG. 3 is a schematic horizontal cross-sectional view of a prior art untapered lens for a dual lens eyewear system.

FIG. 3 schematically illustrates refraction in a prior art lens 41 with circular inside and outside surface horizontal cross-sections, having a uniform thickness 44. With such a lens 41, the angle of incidence of rays from the lens 41 to the eye 46 changes throughout the angular range of vision. For example, a ray which shall be referred to for descriptive purposes as a medial light ray 50 strikes the lens 41 at an angle $\alpha$ to the normal at the point of incidence. As is well known in this art, bending of light at transmitting surfaces depends in part upon the angle of incidence of light rays. The ray 50 is refracted or bent in opposite directions at each of an outer sinner surface 54 inner surface 54 of the lens 41, resulting in a transmitted ray 56 parallel to the incident ray 50. The transmitted ray 50 is laterally displaced, relative to the path of the incident ray 50, by a distance 58. This displacement represents a first order source of optical distortion.

Furthermore, refractory displacement is even more pronounced at a lateral end 60 due to a greater angle of incidence $\beta$. A peripheral incident ray 62 experiences greater displacement 64 than the medial incident ray 50, in accordance with Snell's Law, as will be understood by those of ordinary skill in the optical arts. The discrepancy between the peripheral ray displacement 64 and the medial ray displacement 58 results in a second order of optical distortion. This second order of distortion may cause substantial warping of an image seen through relatively lateral portions of the lens 41.

Figure 4:
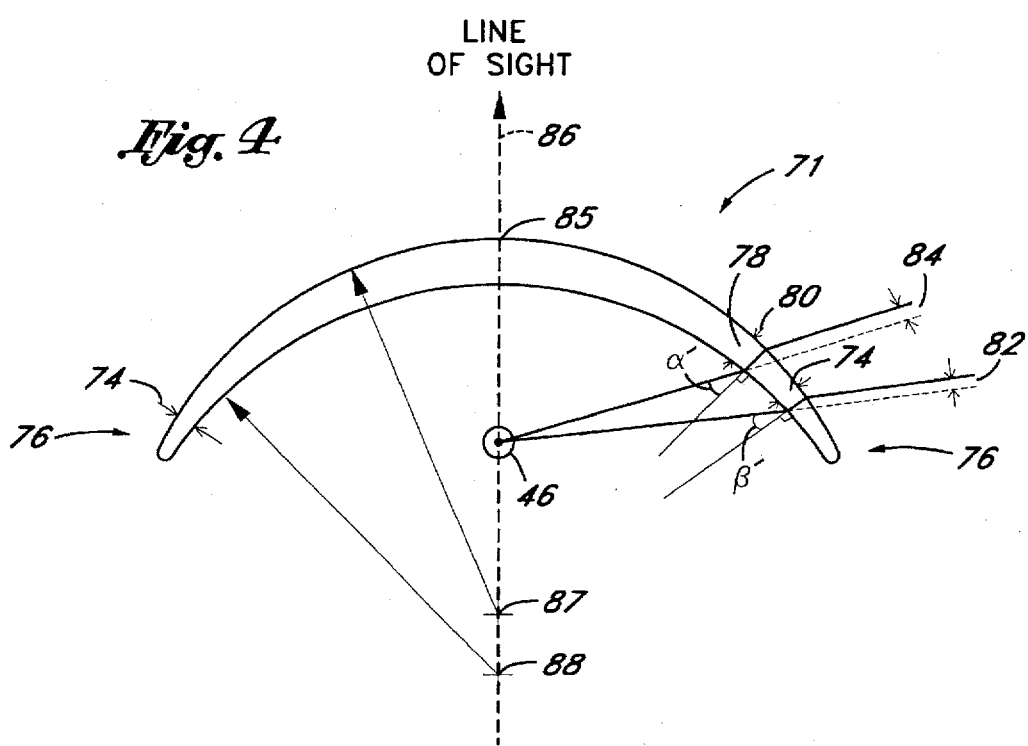
FIG. 4 is a schematic horizontal cross-sectional view of a tapered lens for a dual lens eyewear system.

FIG. 4 schematically illustrates a lens 71 of tapered thickness, to compensate for the greater angle of incidence at the lateral ends 60 of the lens 41 (FIG. 3), as disclosed in the context of unitary lens systems in U.S. Pat. No. 4,859,048, issued to Jannard. Tapering produces a smaller lens thickness 74 at a lateral end 76, relative to a lens thickness 78 at a more medial point 80. This smaller thickness 74 reduces an amount of peripheral ray displacement 82, relative to the peripheral ray displacement 64 through the untapered lens 41 of FIG. 4. In other words, lesser lens thickness 74 near the lateral end 76 of the tapered lens 71 compensates to some extent for a greater angle of incidence $\beta'$, relative to the thickness 78 and angle of incidence $\alpha'$ at the more medial point 80.

The resulting difference between peripheral ray displacement 82 and medial ray displacement 84 on the same lens 71 is not as great as the corresponding difference in FIG. 3, reducing the second order optical distortion. Note that the degree of correction of the second order distortion depends upon a relationship between the manner and degree of tapering from the apex 85 to each lateral end 76 and the manner in which the angle of incidence changes over the same range.

The lens 71 of FIG. 4 is illustrated as though it were mounted within a frame (not shown) such that the wearer's normal line of sight 86 passes perpendicularly through the lens 71 at the lens apex or mechanical center 85. In other words, the angle of incidence to the lens normal is zero for the wearer's normal line of sight. The outer and inner surfaces of lens 71 in the cross-sectional illustration conform to offset, equal-radius circles represented by centerpoints 87 and 88, respectively. A line drawn through centerpoints 87 and 88, referred to herein as the optical centerline of the lens, is collinear with the normal line of sight in the as-worn orientation. This conventional configuration shall be defined as a centrally oriented lens, for ease of description. Circumferentially clockwise or counterclockwise of the normal line of sight 86, the angle of incidence to the lens normal increases in a regular fashion from zero at the lens apex 85.

A high degree of wrap may be desirable for aesthetic styling reasons, for lateral protection of the eyes from flying debris, or for interception of peripheral light. Wrap may be attained by utilizing lenses of tight horizontal curvature (high base), such as small-radius spherical lenses, or by mounting each lens in a position which is canted laterally and rearwardly relative to centrally oriented dual lenses. Such canting shifts the normal line of sight 86 out of a collinear relationship with the optical centerline, and changes the optics of the lens. As a result, prior art dual lens eyewear with substantial "wrap" around the sides of a wearer's face has generally been accompanied by some degree of prismatic distortion.

In accordance with the present invention, there is provided an improved optical configuration and method for minimizing prismatic distortion. Though the present invention may be applied to a wide variety of lens shapes and orientations, the invention has particular utility for dual lens eyewear using high base curvature and demonstrating a high degree of wrap in the as-worn orientation.

Figure 5:
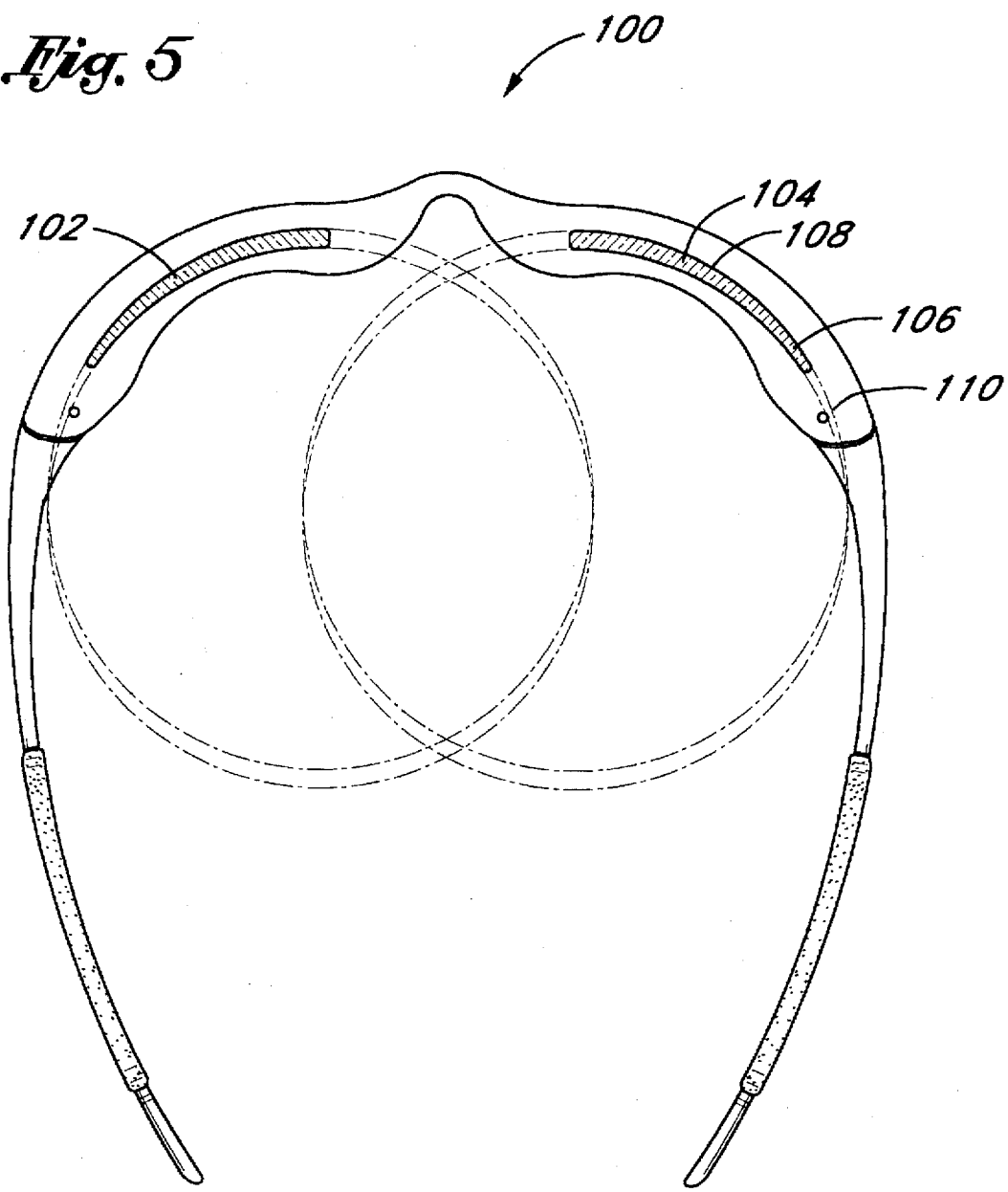
FIG. 5 is a cross-sectional view like that in FIG. 2, showing taper corrected lenses having a greater base curvature, in accordance with another embodiment of the present invention.

Referring to FIGS. 2 and 5, the illustrated eyewear incorporates canted lenses 12 and 14 or 102 and 104, mounted in a position rotated laterally relative to conventional centrally oriented dual lens mountings. A canted lens may be conceived as having an orientation, relative to the wearer's head, which would be achieved by starting with conventional dual lens eyewear having centrally oriented lenses and bending the frame inwardly at the temples to wrap around the side of the head.

As a consequence of the increased wrap, the wearer's normal line of sight 27 no longer strikes the lens 14 perpendicularly, as illustrated in FIG. 4. Instead, the angle of incidence $\theta$ (FIG. 2) for the wearer's line of sight 27 is generally greater than 90°, and to achieve good wrap it may be greater than about 95°, preferably is within the range of from about 100° to about 135°, and in one 9.5 base embodiment is about 101.75°. Lower base lenses generally will exhibit a larger angle $\theta$ in the as worn orientation, and the angle $\theta$ in an embodiment having a base of 6.5 was about 113.4°. In a base 4 embodiment having a pupillary distance of 2.8 inches, the angle $\theta$ was about 119.864°.

FIG. 5 illustrates the horizontal cross-section of an eyeglass 100 in accordance with an embodiment of the present invention, similar in style to that illustrated in FIG. 2, except having lenses 102 and 104 of tighter curvature (higher base) as well as possibly greater wrap. When the eyeglass 100 is worn, a lateral edge 106 of the lens 104 wraps significantly around and comes in close proximity to the wearer's temple to provide significant lateral eye protection as has been discussed.

An anterior (front) surface 108 of the lens of the present invention will generally conform to a portion of the surface of a regular geometric solid, such as a sphere 110, shown here horizontal cross-section. The front surfaces of spherical lenses 102 and 104 of the illustrated embodiment can, therefore, be characterized by a radius. By convention in the industry, the curvature may also be expressed in terms of a base value, such that the radius (R) in millimeters of the anterior surface of the lens is equal to 530 divided by the base curve, or $$R = 530/B \qquad (1)$$

The present invention provides the ability to construct dual lens eyeglass systems having relatively high wrap using lens blanks having a base curve of 6 or greater, preferably between about 7½ and 10½, more preferably between about 8 and 9½, and, in one embodiment between about 8¾ and 9. The radius of the circle conforming to the anterior surface of a base 8¾ lens, for example, is about 60.57 millimeters. For comparison, the radius of the circle which characterizes the anterior surface of a base 3 lens is about 176.66 millimeters.

The embodiment of the present invention illustrated in FIG. 5 may be cut from a base 8¾ lens blank having a thickness of about 0.0649 inches at the optical centerline and about 0.053 inches at reference a point two inches along the outer circumference of the lens from the optical centerline. Alternatively, the lens can be molded directly into its final shape and configuration.

Figure 6:
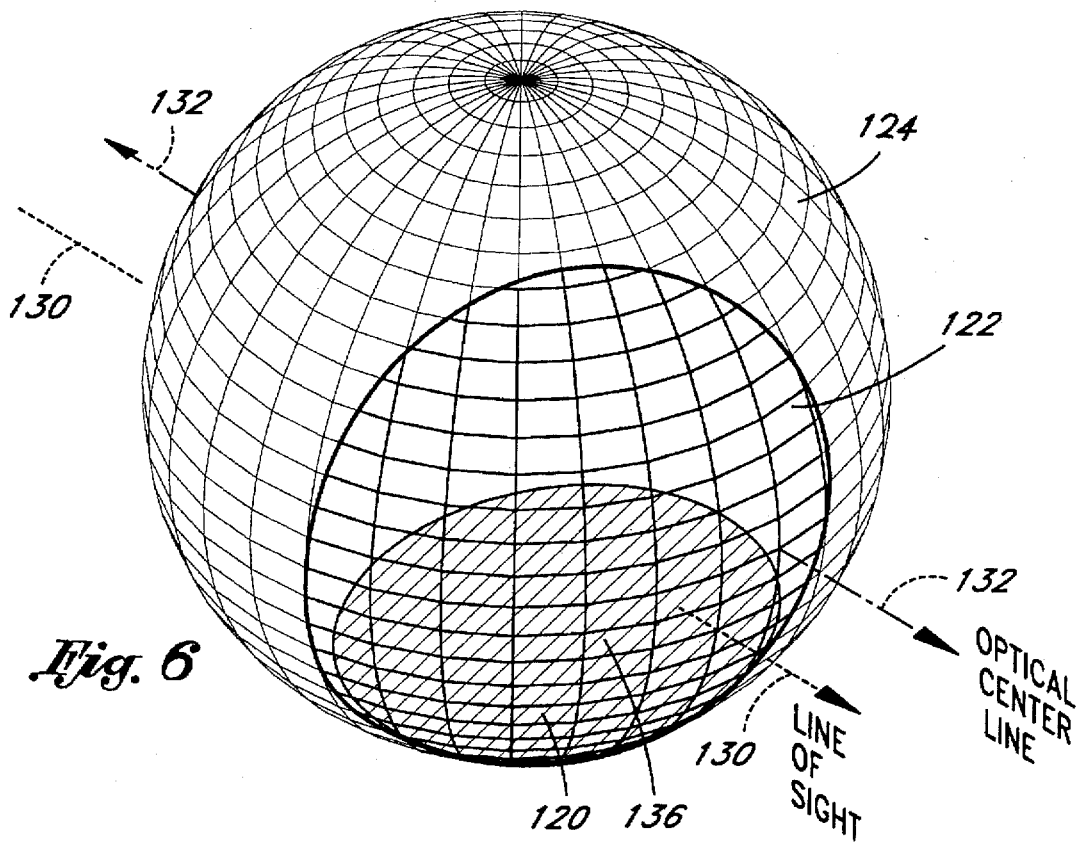
FIG. 6 is a perspective view of a lens blank conforming to a portion of the surface of a sphere, showing a lens profile to be cut from the blank in accordance with a preferred embodiment of the present invention.

FIG. 6 is a perspective view of a lens blank 122, a convex outside surface 136 of which generally conforms to a portion of the surface of a three-dimensional geometric shape 124. It will be understood by those of skill in this art that lenses in accordance with the present invention may conform to any of a variety of geometric shapes.

Preferably, the outside surface of the lens will conform to a shape having a smooth, continuous surface having a constant horizontal radius (sphere or cylinder) or progressive curve (ellipse, toroid or ovoid) in either the horizontal or vertical planes. The geometric shape 124 of the preferred embodiments herein described, however, generally approximates a sphere.

Figure 7:
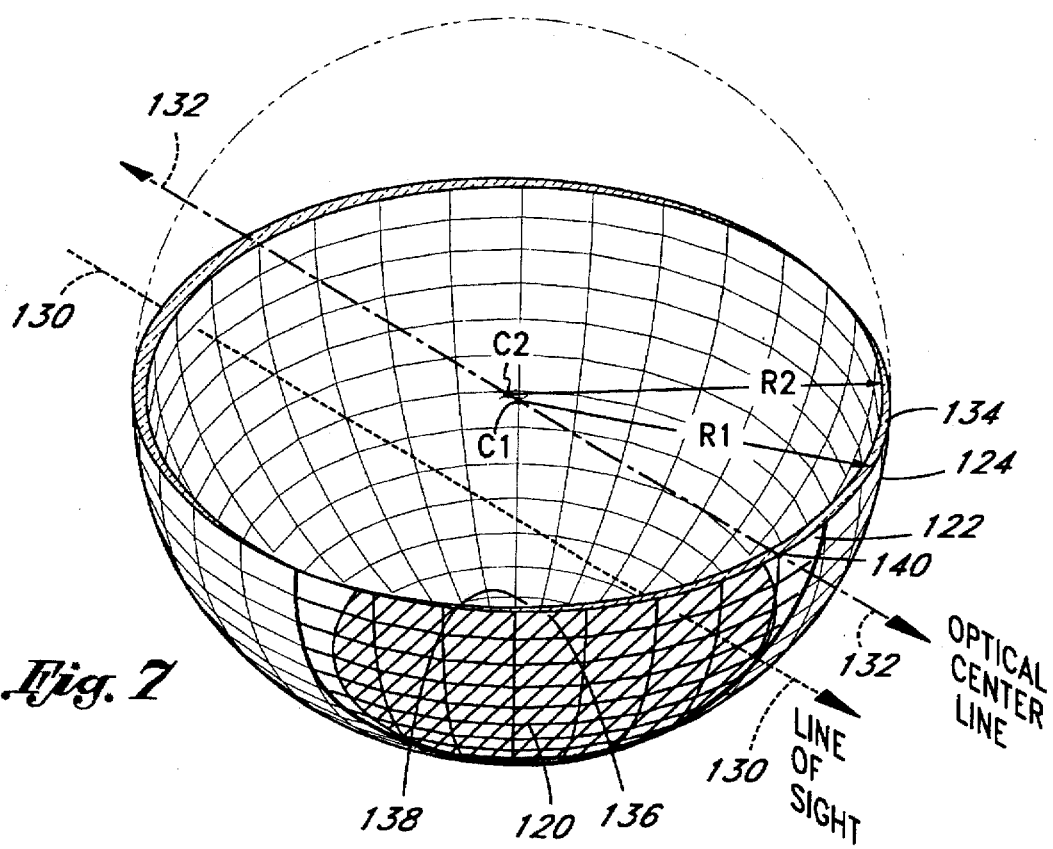
FIG. 7 is a perspective cutaway view of the hollow, tapered wall spherical shape, lens blank, and lens of FIG. 6.

The sphere 124 illustrated in FIGS. 6 and 7 is an imaginary three-dimensional solid, a portion of the wall of which is suitable from which to cut a lens 120. As is known in the art, precision lens cutting is often accomplished by producing a lens blank 122 from which a lens 120 is ultimately cut. However, it should be clear to those of skill in the art from the illustrations of FIGS. 6 and 7, that the use of a separate lens blank is optional, and the lens 120 may be molded directly into its final shape and configuration if desired.

It can also be seen from FIGS. 6 and 7 that the lens 120 and/or the lens blank 122 can be positioned at any of a variety of locations along the sphere 124. For the purpose of the present invention, the optical centerline 132 operates as a reference line for orientation of the lens 120 with respect to the sphere 124. In the illustrated embodiment, wherein both the outside surface and the inside surface conform to a portion of a sphere, the optical centerline is defined as the line 132 which joins the two centers C1 and C2. The analogous reference line for the purpose of nonspherical lens geometry may be formed in a manner different than connection of the two geometric centers of the spheres, as will be apparent to one of skill in the art.

The lens 120 is ultimately formed in such a manner that it retains the geometry of a portion of the wall of the sphere as illustrated in FIG. 7. The location of the lens 120 on the sphere 124 is selected such that when the lens 120 is oriented in the eyeglass frame, the normal line of sight 130 of the wearer through the lens will be maintained generally in parallel to the optical centerline 132 of the geometric configuration from which the lens 120 was obtained. In the illustration of FIGS. 6 and 7, the lens 120 is a right lens which has a significant degree of wrap, as well as some degree of rake. A lens having a different shape, or a lesser degree of wrap may overlap the optical centerline 132 of the imaginary sphere 124 from which the lens was formed. However, whether the optical centerline of the imaginary sphere 124 crosses through the lens 120 or not is unimportant, so long as the line of sight 130 in the lens 120 is maintained generally in parallel in the as-worn orientation with the optical centerline 132.

For purposes of the present invention, "substantially parallel" shall mean that the line of sight 130 when the lens 120 is oriented in the as worn position generally does not deviate within the horizontal plane by more than about ±15° from parallel to the optical centerline 132. Preferably, the normal line of sight 130 should not deviate by more than about ±10° from the optical centerline 132, more preferably the normal line of sight 130 deviates by no more than about ±5° and most preferably no more than about ±2° from parallel to the optical centerline 132. Optimally, the line of sight 130 is parallel to the optical centerline in the as worn orientation. Typically, an eyewear frame has a vertical plane of symmetry which is substantially parallel to the line of sight 130. Accordingly, the optical centerline 132 will be substantially parallel to the frame's vertical plane of symmetry.

Variations from parallel an the horizontal plane generally have a greater negative impact on the lens than variations from parallel in the vertical plane. Accordingly, the solid angle between the line of sight 130 and optical centerline 132 in the vertical plane may exceed the ranges set forth above, for some eyewear, as long as the horizontal component of the angle of deviation is within the above-mentioned ranges of deviation from the parallel orientation. Preferably, the line of sight 130 deviates in the vertical plane no more than about ±10° and, more preferably, no more than about ±3° from the optical centerline in the as worn orientation.

FIG. 7 is a cutaway view of the lens 120, lens blank 122, and geometric shape 124 of FIG. 6. This view shows that the preferred geometric shape 124 is hollow with walls of varying thickness, as revealed by a horizontal cross-section 134 at the optical centerline of the geometric shape 124.

The tapered walls of the preferred geometric shape 124 result from two horizontally offset spheres, represented by their center points C1 and C2 and radii R1 and R2. An outer surface 136 of the preferred lens blank 122 conforms to one sphere (of radius R1) while an inner surface 138 of the lens blank 122 conforms to the other sphere (of radius R2). By adjusting the parameters which describe the two spheres, the nature of the taper of the lens blank 122 may also be adjusted.

In particular, the parameters for the two spheres to which the lens blank outer surface 136 and inner surface 138 conform is preferably chosen to produce zero refractive power, or non-prescription lenses. Where CT represents a chosen center thickness (maximum thickness of the wall of the hollow geometric shape 124), n is an index of refraction of the lens blank material, R1 is set by design choice for the curvature of the outer surface 136, R2 may be determined according to the following equation:

$$R_2 = R_1 - CT + \frac{CT}{n} \qquad (2)$$

CT/n represents the separation of the spherical centers C1 and C2. For example, where a base 6 lens is desired as a matter of design choice, the center thickness is chosen to be 3 mm, and the index of refraction of the preferred material (polycarbonate) is 1.586, R2 may be determined as follows:

$$R_2 = \frac{530}{6} - 3 + \frac{3}{1.586} = 87.225 \text{ mm} \quad (3)$$

For this example, the radius R1 of the outer surface 136 is equal to 88.333 mm, the radius R2 of the inner surface 138 is equal to 87.225 mm, and the spherical centers C1 and C2 are separated by 1.892 mm. These parameters describe the curvature of the lens blank 122 of the preferred embodiment.

In the case of the preferred embodiment, the optical centerline 132 is that line which passes through both center points C1 and C2 of the offset spheres. This happens to pass through the thickest portion of the preferred geometrical shape 124 walls at an optical center 140, though this may not be true for alternative nonspherical embodiments. The optical center 140 happens to pass through surface 136 of the illustrated lens blank 122, although this is not necessary. The optical center 140 does not happen to lie on the lens 120, although it may for larger lenses or lenses intended to exhibit less wrap in the as-worn orientation.

Figure 8:
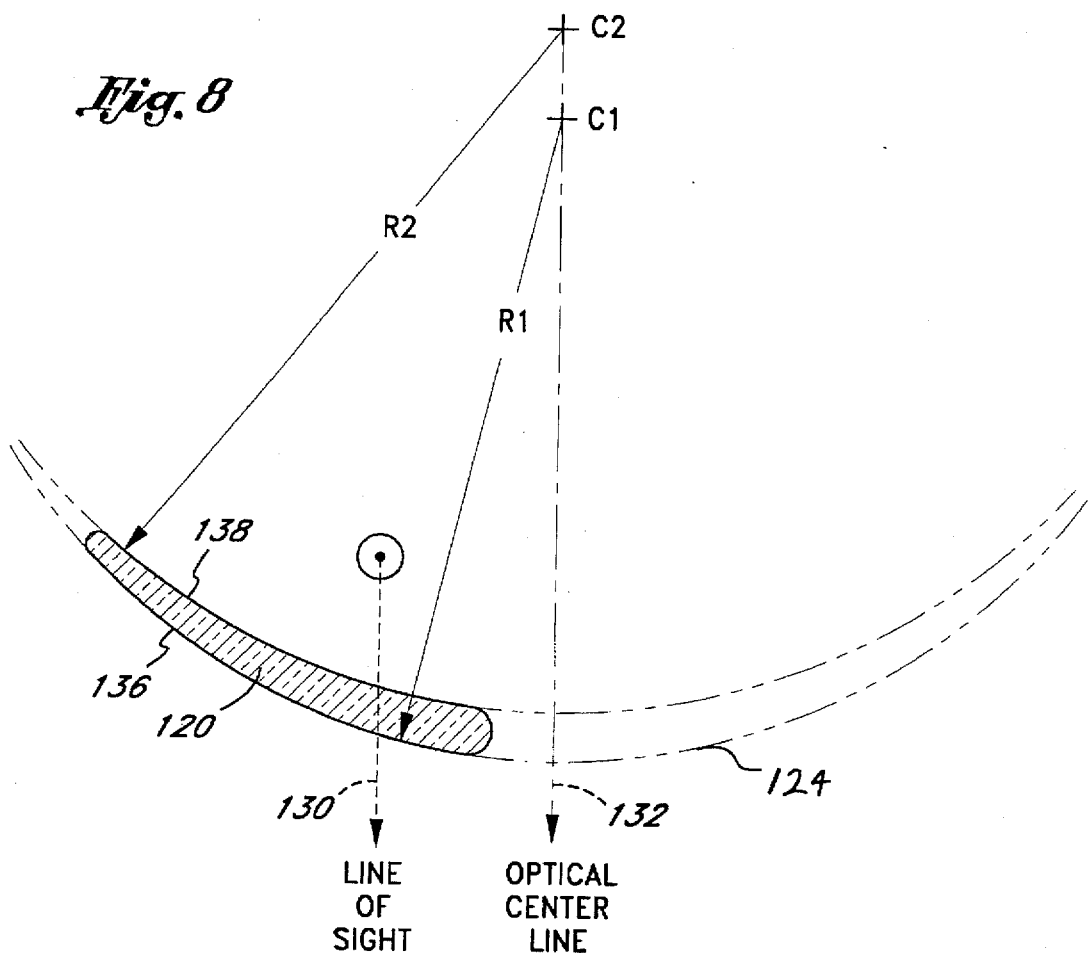
FIG. 8 is a horizontal cross-sectional view of a lens constructed in accordance with a preferred embodiment of the present invention.

FIG. 8 illustrates a horizontal cross-section of the preferred lens 120, showing in phantom the geometric shape 124 to which the outer surface 136 and inner surface 138 conform. The lens blank 122 is omitted from this drawing. In accordance with the present invention, the optical centerline 132 associated with the chosen taper is aligned to be parallel with the normal line of sight 130 of the wearer as the lens 120 is to be mounted in an eyeglass frame.

Furthermore, although the preferred embodiments are circular in both horizontal and vertical cross-section, a variety of lens configurations in both planes are possible in conjunction with the present invention. Thus, for example, the outer surface of the lens of the present invention may generally conform to a spherical shape as shown in FIGS. 6 and 7. Alternatively the lens may conform to a right circular cylinder, a frusto-conical, an elliptic cylinder, an ellipsoid, an ellipsoid of revolution, or any of a number of other three dimensional shapes. Regardless of the particular vertical or horizontal curvature of the outer surface, however, the inner surface should be chosen such as to smoothly taper the lens thickness at least in the horizontal plane.

FIGS. 9–12 will aid in describing a method of choosing a location on the lens blank 122 from which to cut the right lens 120, in accordance with a preferred embodiment of the present invention. It will be understood that a similar method would be used to construct the left lens for the dual lens eyewear of the preferred embodiment.

As a first step, a desired general curvature of the lens outer surface 136 may be chosen. For the preferred lens 120, this choice determines the base value of the lens blank 122. As noted elsewhere herein, a number of other curvatures may be utilized in conjunction with the present invention. A choice of lens thickness may also be preselected. In particular, the minimum thickness may be selected such that the lens will withstand a preselected impact force.

A desired lens shape may also be chosen. For example, FIG. 12 illustrates an example of a front elevational shape for the lens 120. The particular shape chosen is generally not relevant to the decentered lens optics disclosed herein.

Figure 9:
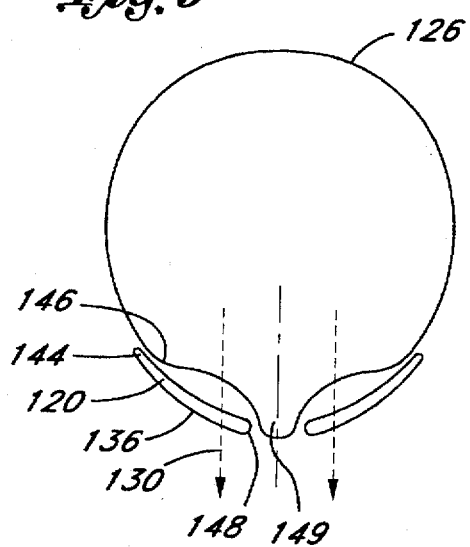
FIG. 9 is a top plan view of the lens of FIG. 8 showing a high wrap in relation to a wearer.
Figure 10:
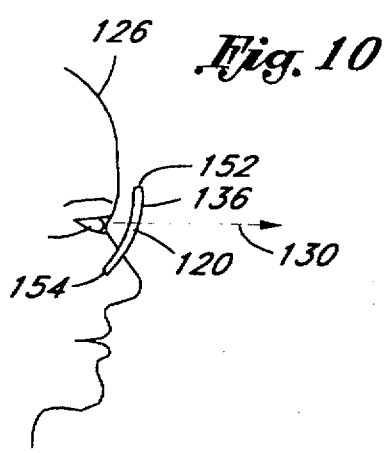
FIG. 10 is a right side elevational cross-section of the lens and wearer of FIG. 9, showing lens rake.

A desired as-worn orientation for the lens should also be chosen, relative to the normal line of sight 130 of the wearer 126. As mentioned above, preferred orientations may provide significant lateral wrap for lateral protection and interception of peripheral light, and for aesthetic reasons. For example, the embodiment illustrated in FIGS. 6–12 uses a canted lens 120 to achieve wrap. Alternatively, wrap may be achieved through use of a higher base lens and a more conventional (non-canted) orientation. FIGS. 9 and 10 illustrate more plainly how the orientations may be related to the line of sight 130 of the wearer.

The eyewear designer may also choose a degree of rake, or vertical tilt, as will be understood from FIG. 10, schematically illustrating the vertical orientation of the lens 120 relative to the head of the wearer 126, and relative in particular to the normal line of sight 130. A downward rake, as illustrated, is desirable for a variety of reasons, including improved conformity to common head anatomy. As will be apparent to those of skill in the art, a lens 120 having a mechanical center point which falls below the horizontal plane intersecting the optical centerline 132 (see FIG. 7) will tend to have a downward rake as illustrated in FIG. 10. This is because the lens 120 will have been formed below the equator of the sphere relative to the optical centerline. Since the orientation of the lens 120 to the optical centerline 122 in the imaginary sphere should be the same as the orientation between the lens 120 and a parallel to the normal line of sight 130 in the as-worn condition, any lens cut from this sphere below the optical centerline 132 should exhibit a corresponding degree of downward rake.

Figure 11:
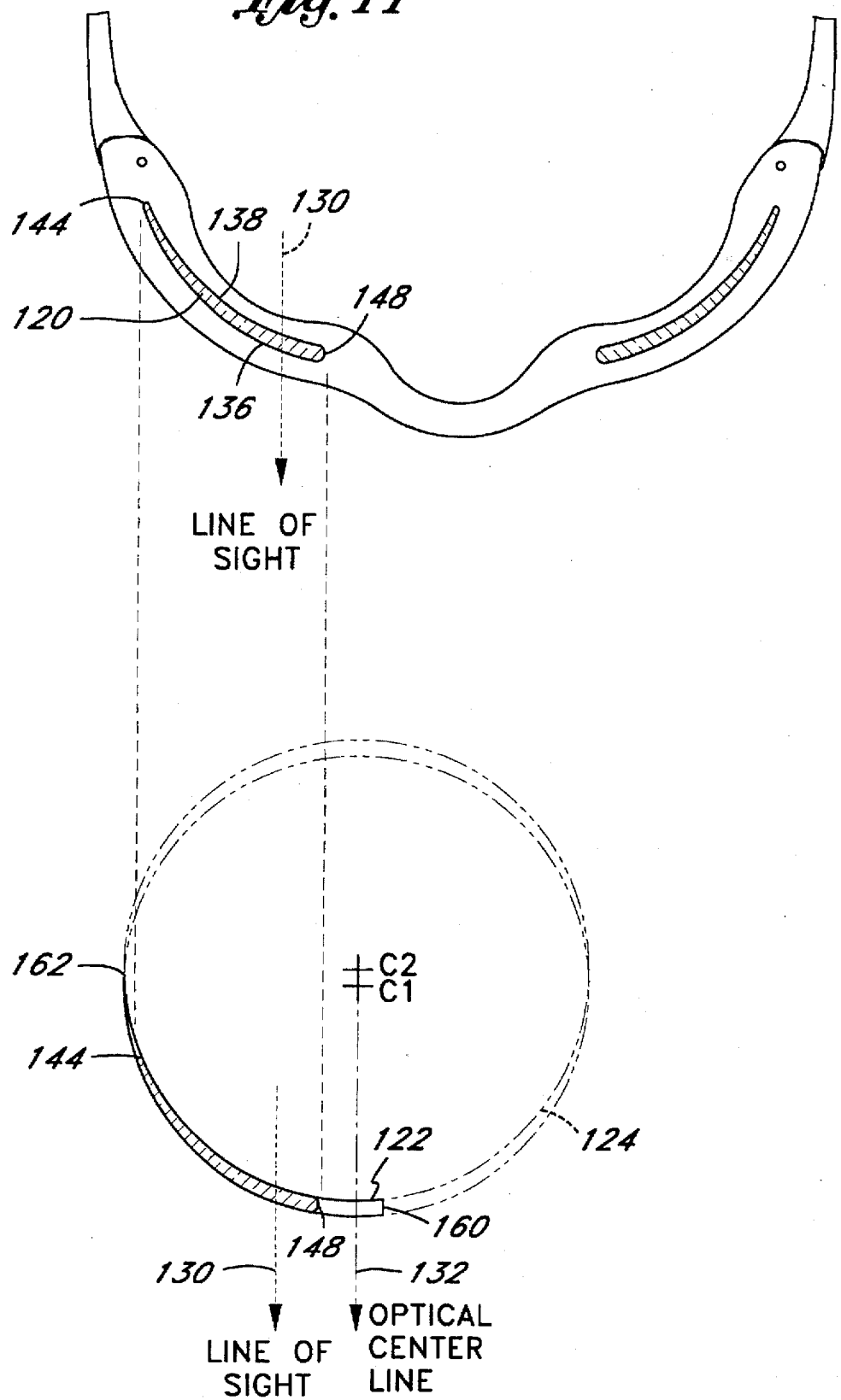
FIG. 11 schematically illustrates the projection of the lens profile from a desired orientation within an eyewear frame to the lens blank in accordance with a preferred embodiment of the present invention.

Referring now to FIG. 11, a mapping of the horizontal orientation of the lens 120 onto the lens blank 122 is illustrated. The normal line of sight 130, with respect to which the chosen orientation is measured, is maintained substantially parallel to the optical centerline 132.

Once the aesthetic design such as that illustrated in FIG. 11 has been determined, and the lens blank 122 formed having a suitable base curvature for fitting within the aesthetic design, the aesthetic design may be "projected" onto the surface of the sphere to reveal that portion of the sphere which is suitable for use as the lens 120. The projection of the lens shape onto the sphere should be moved about the surface of the sphere until it is positioned such that the lens cut from the sphere at that location will exhibit the appropriate wrap and rake for the aesthetic design without any rotation of the lens 120 out of its orientation in which the optical centerline of the sphere is generally parallel to the normal line of sight in the as-worn orientation.

Although not illustrated, it will be understood that a similar projection may be performed for the vertical orientation chosen, as depicted in FIG. 10, for instance. FIG. 10 provides reference points in the form of the lens top edge 152 and bottom edge 154 in relation to the line of sight 130. The projection may then be shifted up or down until the top edge 152 and the bottom edge are both simultaneously aligned with corresponding points on the outer surface 136 of the lens blank, while maintaining the line of sight 130 substantially parallel with the optical centerline 132.

Projection of both the horizontal profile and the vertical profile may be performed simultaneously, locating a unique position on the lens blank 122 corresponding to the desired three-dimensional shape of the lens (including the front elevational shape shown in FIG. 12) at which the line of sight 130 is parallel to the optical centerline 132 or other reference line of the lens blank 122. Of course, it will be understood that the lines 130 and 132 may be substantially parallel, that is, within the acceptable range of angular deviation set forth above.

This shape may then be cut from the blank 122 or molded directly in the final lens configuration. The resultant lens 120 not only conforms to the desired shape, but also minimizes prismatic distortion.

FIG. 12 illustrates a lens blank 122, such as that shown conforming to a portion of the surface of the sphere in FIGS. 6 and 7. In FIG. 12, the lens blank 122 has been rotated such that the mechanical center of the blank is illustrated in the center of the drawing. The illustrated lens 120 has a medial edge 148, a lateral edge 144, an upper edge 152 and a lower edge 154. At least a portion of the right lens 120 lies in the lower left-hand (third) quadrant of the lens blank 122. Preferably, in an embodiment of the invention exhibiting both wrap and downward rake, at least about half of the lens area will fall within the third quadrant of the lens blank 122. Preferably all or substantially all of the area of the lens 120 will lie below and to the left of the optical center as illustrated. Lenses exhibiting a similar degree of rake but lesser wrap may be positioned on the lens blank 122 such that as much as 50% or more of the lens area is within the lower right (second) quadrant of the lens blank 122.

The present invention thus provides a precise method of furnishing the correct correspondence between taper and the varying angle of incidence from the wearer's eye to the surface of a lens. By recognizing a novel relationship among the wearer's line of sight and the form of taper, the present invention allows use of any of a variety of lens designs while minimizing prismatic distortion. For example, a designer may choose a desirable orientation and curvature for the lens, relative to a wearer's line of sight. The orientation and curvature may be chosen from a wide range of rake (i.e., vertical "tilt" of the lens), horizontal cant, base value and proximity to a wearer's face, including those parameters resulting in a high degree of wrap. The form of taper may then be chosen, by the method of the present invention, such that the prismatic distortion is minimized.

Although the foregoing invention has been described in terms of certain preferred embodiments, other embodiments will become apparent to those of ordinary skill in the art in view of the disclosure herein. Accordingly, the present invention is not intended to be limited by the recitation of preferred embodiments, but is intended to be defined solely by reference to the appended claims.

What is claimed:

1. A method of manufacturing a right lens for dual lens optically corrected eyewear exhibiting wrap and downward rake, the method comprising:

providing a lens blank, the lens blank having a thickness which is vertically tapered symmetrically on either side of a central equatorial line and horizontally tapered from a relatively greater thickness at an optical center located between the geometric center of the blank and a medial edge of the blank to a relatively lesser thickness at a lateral edge of the blank, the equatorial line dividing the lens blank into an upper half and a lower half; and cutting the right lens from the lens blank such that greater than 50% of the right lens is cut from the lower half.

2. The method of claim 1, greater than about 50% of the lens is cut from the lower lateral quadrant.

3. The method of claim 1, wherein the optical center lies outside the right lens.

4. A method of manufacturing noncorrective, dual lens eyewear exhibiting wrap and downward rake, the method comprising:

obtaining a lens blank comprising an inner surface conforming to a first sphere having a first center, and an outer surface conforming to a second sphere having a second center offset from the first center, a vertically and horizontally tapered lens thickness defined between the inner and outer surfaces, and an optical centerline passing through the first and second centers;

selecting a desired lens shape;

selecting a desired lens orientation relative to a wearer's normal line of sight;

projecting the desired lens shape onto the lens blank;

cutting a lens having the desired lens shape from a preselected location on the lens blank which location relates to the desired lens orientation;

mounting the lens in a frame such that the optical centerline is vertically spaced from and substantially parallel with the wearer's theoretical normal straight ahead line of sight.

5. The method of claim 4, wherein the optical centerline is horizontally spaced from the wearer's normal line of sight.

6. The method of claim 4, wherein the optical centerline deviates by no more than about ±10° from parallel with the normal line of sight.

7. The method of claim 6, wherein the optical centerline deviates within a vertical plane by no more than about ±3° from parallel with the normal line of sight and deviates within a horizontal plane by no more than about ±2°.

8. A method of manufacturing optically corrected, non-power eyewear, comprising the steps of:

providing a lens blank having a thickness which tapers in both a vertical and horizontal plane, and having an optical centerline;

providing an eyeglass frame configured to maintain at least one lens in a predetermined relationship with respect to a wearer's reference line of sight when the eyewear is worn on the head of the wearer;

cutting a lens from a location on the lens blank such that the optical centerline is maintained generally parallel with the reference line of sight when the lens is supported by the eyeglass frame and worn on the head of the wearer; and attaching the lens to the eyeglass frame to produce optically corrected eyewear.

9. A method of manufacturing optically corrected non-power eyewear as in claim 8, wherein the attaching step comprises attaching a unitary lens to the eyeglass frame.

10. A method of manufacturing optically corrected non-power eyewear as in claim 8, wherein the attaching step comprises attaching two lenses to the eyeglass frame.

11. A method of manufacturing optically corrected non-power eyewear as in claim 8, wherein the wearer's reference line of sight is the wearer's straight ahead normal line of sight.

12. A method of manufacturing optically corrected non-power eyewear as in claim 8, wherein the cutting step comprises cutting a lens from a position on the lens blank such that the geometric center of the lens is displaced from the geometric center of the lens blank in both a vertical and a horizontal plane.

13. A method as in claim 8, wherein said providing step comprises providing an eyeglass frame configured to maintain at least one lens in the predetermined relationship with respect to the wearer's reference line of sight, in which relationship the lens has both rake and wrap.

14. A method in claim 8, wherein the wearer's normal line of sight deviates, within the horizontal plane by no more than about plus or minus 2° from parallel with the optical centerline.

15. The method of claim 8, wherein the wearer's normal line of sight deviates in the vertical plane by no more than about plus or minus 3° from parallel with the optical centerline.

* * * * *